US009655773B2

(12) United States Patent
Kontur et al.

(10) Patent No.: US 9,655,773 B2
(45) Date of Patent: May 23, 2017

(54) DEVICE FOR INJECTING AN INTRAOCULAR LENS INTO AN EYE

(71) Applicant: MEDICONTUR ORVOSTECHNIKAI KORLÁTOLT FELELŐSSÉGŰ TÁRSASÁG, Zsámbék (HU)

(72) Inventors: Laszlo Kontur, Munich (HU); Nandor Turkevi-Nagy, Zsambek (HU); Attila Stefan, Telki (HU)

(73) Assignee: MEDICONTUR ORVOSTECHNIKAI KORLATOLT FELELOSSEGU TARSASAG, Zsambek (HU)

( * ) Notice: Subject to any disclaimer, the term of this patent is extended or adjusted under 35 U.S.C. 154(b) by 679 days.

(21) Appl. No.: 14/344,750

(22) PCT Filed: Sep. 17, 2012

(86) PCT No.: PCT/EP2012/068277
§ 371 (c)(1),
(2) Date: Mar. 13, 2014

(87) PCT Pub. No.: WO2013/038021
PCT Pub. Date: Mar. 21, 2013

(65) Prior Publication Data
US 2015/0045805 A1 Feb. 12, 2015

(30) Foreign Application Priority Data
Sep. 16, 2011 (FR) ...................................... 11 58252

(51) Int. Cl.
*A61F 2/16* (2006.01)
*A61F 9/00* (2006.01)

(52) U.S. Cl.
CPC .......... *A61F 9/0017* (2013.01); *A61F 2/1678* (2013.01)

(58) Field of Classification Search
CPC .... A61F 9/0008; A61F 9/0017; A61F 2/1662; A61F 2/167; A61F 2/1675; A61F 2/1678; A61F 2/1672
See application file for complete search history.

(56) References Cited

U.S. PATENT DOCUMENTS 6,203,549 B1 * 3/2001 Waldock ................. A61F 2/167
606/107
2003/0036765 A1 2/2003 Van Noy
(Continued)

FOREIGN PATENT DOCUMENTS

BE 1 016 692 A3 4/2007
DE 202 21 644 U1 10/2006
FR 2 808 993 A1 11/2001

OTHER PUBLICATIONS

International Search Report, dated Jan. 2, 2013, from corresponding PCT application.
(Continued)

*Primary Examiner* — Jonathan Miles
(74) *Attorney, Agent, or Firm* — Ipsilon USA, LLP

(57) ABSTRACT

An injection assembly for a flexible intraocular lens, includes an injector body (1) accommodating a sliding push member (2), and a compaction and ejection chamber (3) rigidly connected to the injector body. The injection assembly includes a cartridge (6) receiving an intraocular lens (7) in a non-stressed state, the cartridge (6) being stored separately in a sterile container (32), and the compaction and injection chamber (3) is pivotably connected to the distal end of the injector body so as to be capable of occupying two positions, namely: a cartridge-loading position, in which the chamber is folded along the injector body, and an injection
(Continued)

position, in which the chamber is aligned with the injector body. A tab (4) makes it possible to release the push member (2) when the tab is placed in a position for locking the compaction and injection chamber in a closed position on the injector body.

19 Claims, 6 Drawing Sheets

(56) References Cited

U.S. PATENT DOCUMENTS

2005/0251236 A1 11/2005 Jeannin et al.
2008/0058830 A1 3/2008 Cole et al.
2009/0125034 A1 5/2009 Pynson

OTHER PUBLICATIONS

French Search Report, dated Apr. 3, 2012, from corresponding French application.

* cited by examiner

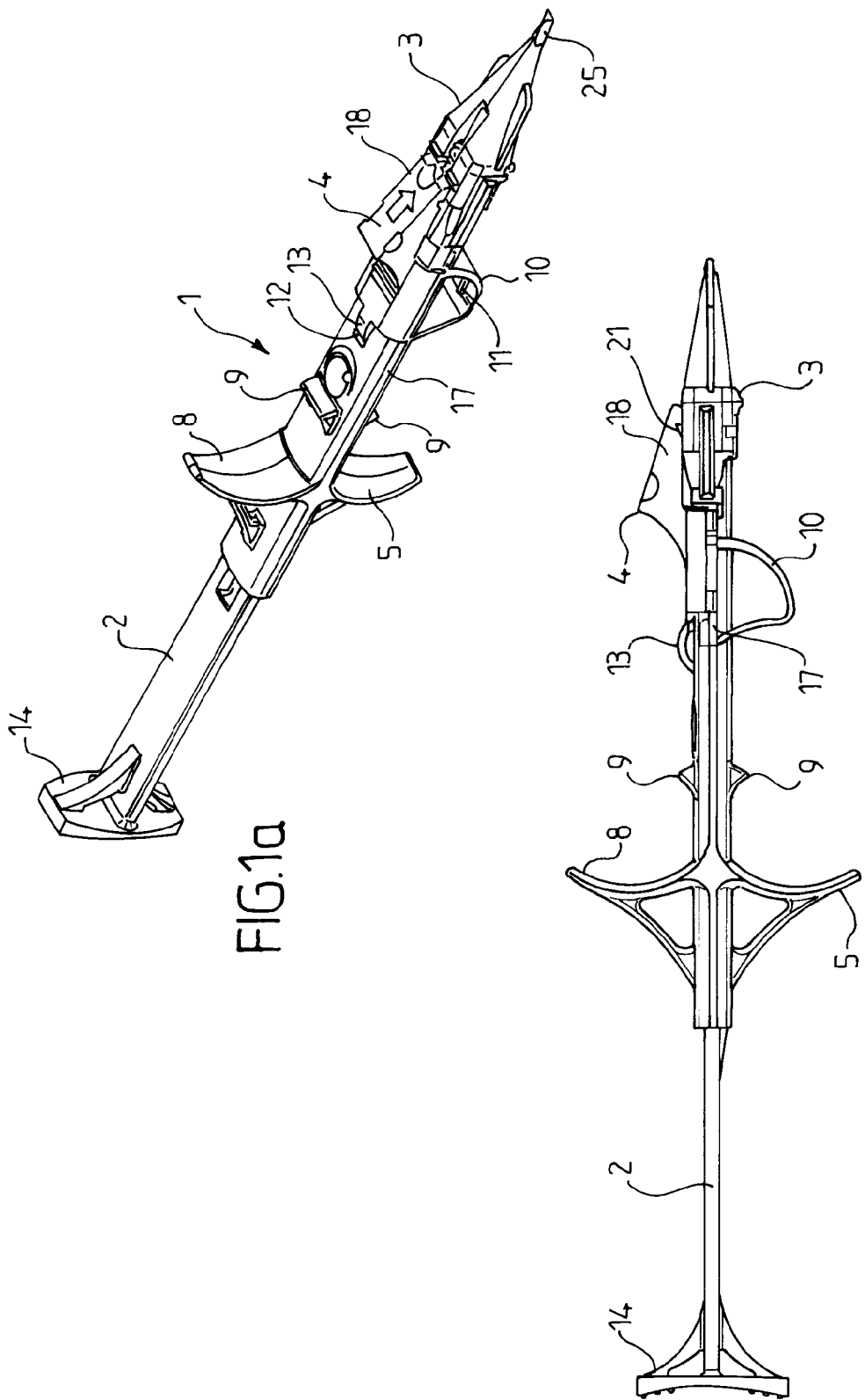

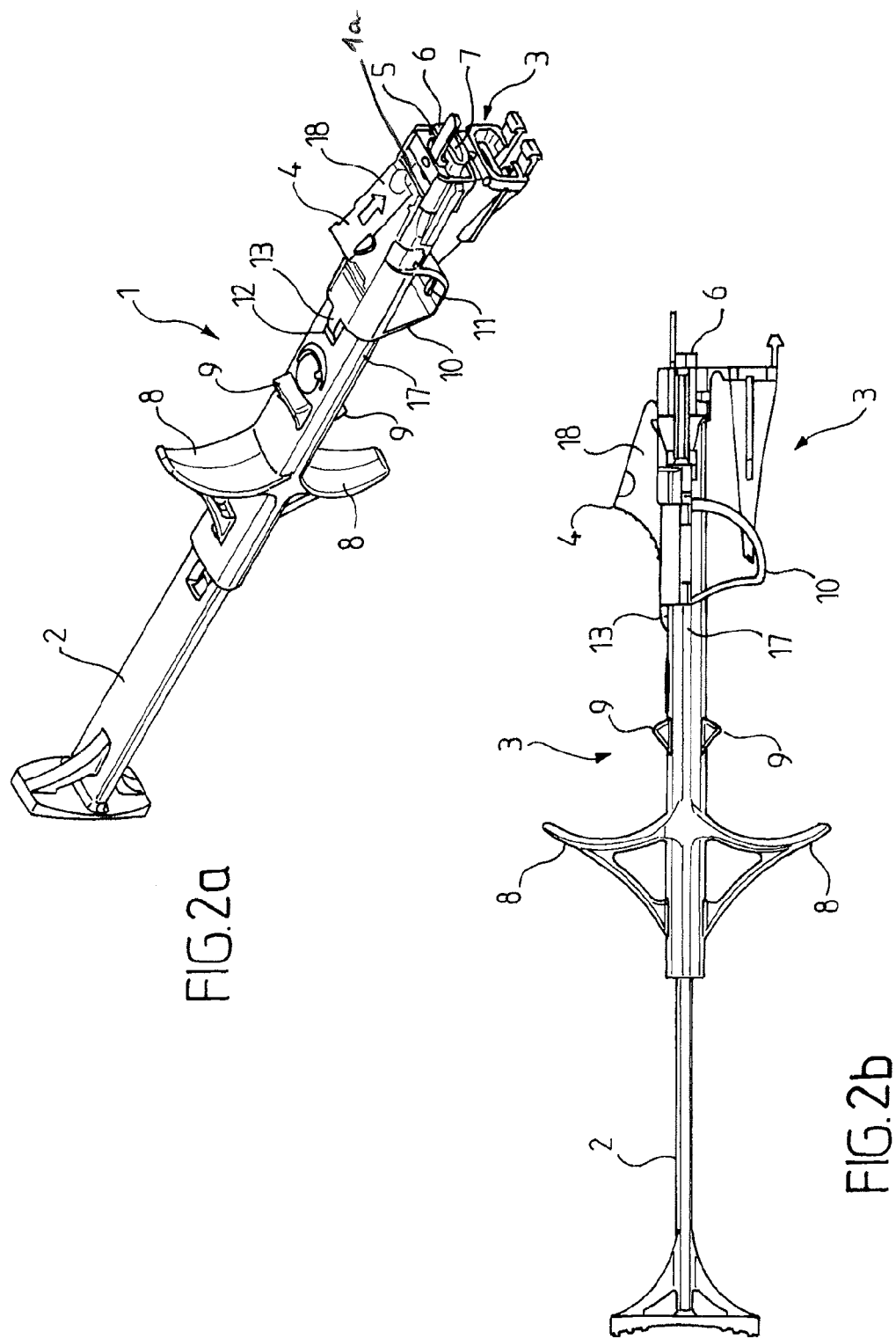

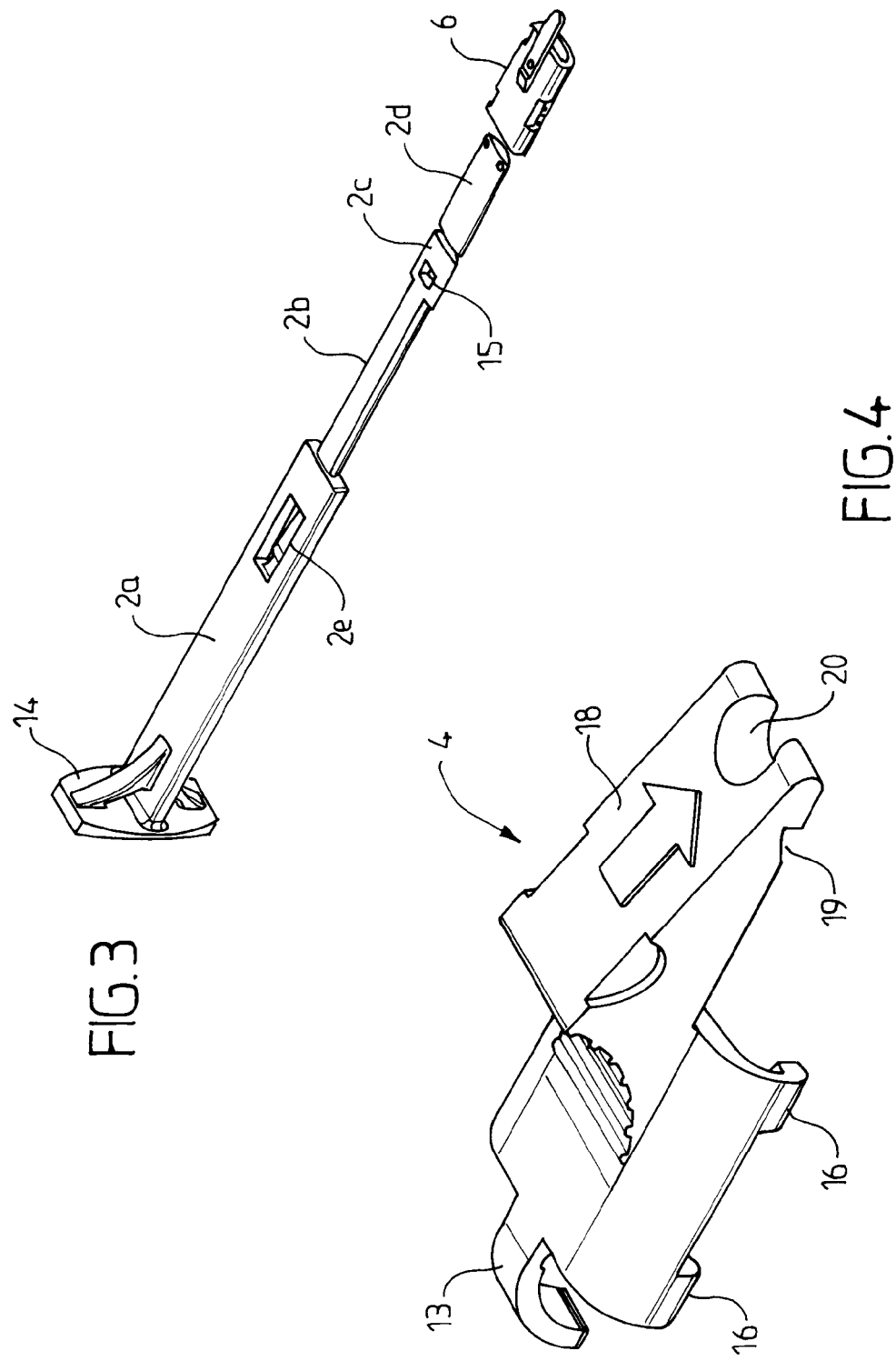

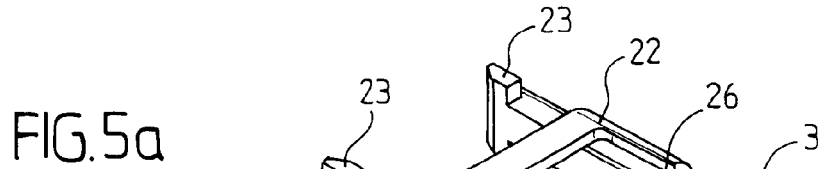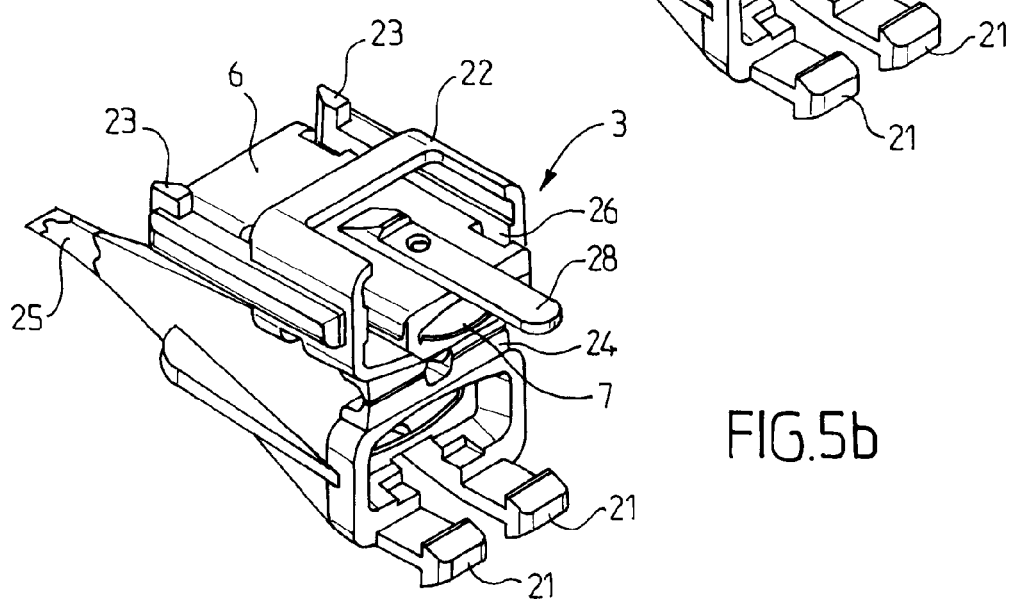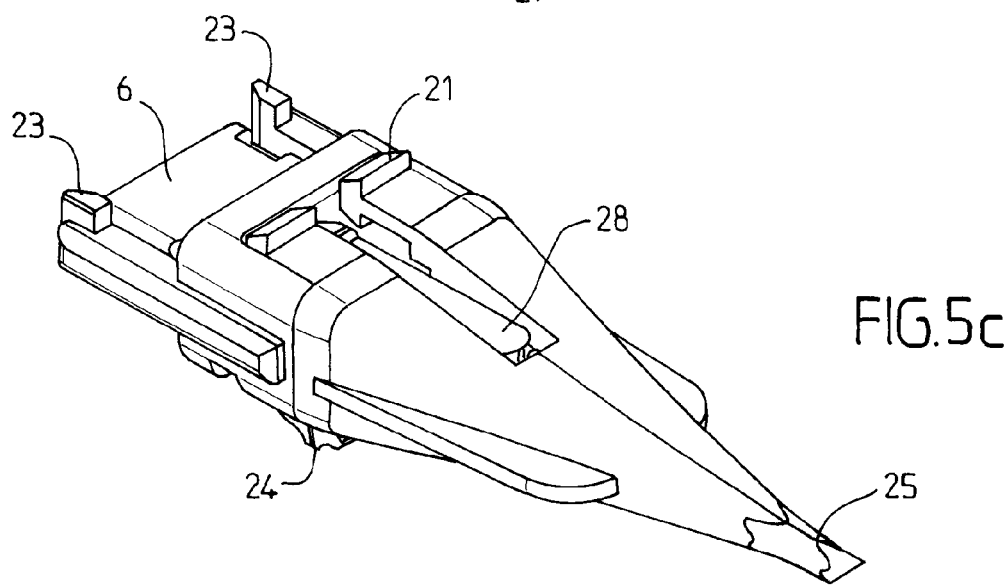

DEVICE FOR INJECTING AN INTRAOCULAR LENS INTO AN EYE

The invention relates to devices for injecting an intraocular lens, hereinafter IOL, into an eye.

It is nowadays common to inject into the eye flexible and foldable IOLs made of materials such as silicone, flexible acrylics or hydrogels, which means that only a self-suturing incision of the order of 3 mm has to be made in the eye when implanting the IOL.

To this end, numerous injection devices have been proposed. They are generally composed of a cartridge in which the IOL is folded and which is fitted on a syringe-type injector of which the output end is shaped as a cannula of small diameter, the pusher of the injector forcing the expulsion of the IOL through said cannula.

To ensure that the IOL folds correctly without risk of deformation or pinching, various improved cartridge devices have been designed, of which an example is described in the document FR 2 808 993. According to said document, the cartridge is designed in such a way as to form a folder module which comprises two jaws that are movable relative to each other, each jaw having a folder wall constituted by a portion of a cylindrical surface and a plane wall secured to the folder wall, the two plane walls being arranged in parallel planes. An axis of rotation orthogonal to the plane walls controls the relative rotation movement of one jaw relative to the other. One of the jaws can occupy three positions relative to the other jaw: a first position, in which the plane walls are offset from each other, the IOL being placed on the lower plane wall; a second position, in which the plane walls face each other, the plane walls and the folder walls defining a confinement volume for the implant; and a third position, in which the folder walls meet each other so as to define a substantially cylindrical volume forming a folder chamber. The folder module is designed to constitute a storage chamber for the IOL in the non-stressed state before its use, and to be fitted on the injector at the time of said use. However, it means that the surgeon has to fold the IOL by acting on the movable jaws of the folder module before carrying out the injection. Moreover, the injector as a whole has to be sterilized and stored in a package containing a storage liquid such as pure water or a saline aqueous solution. For this reason, the packages are bulky and relatively heavy, and therefore expensive to dispatch, and, when the surgeon opens them to use an injector, the latter is wet, making it awkward to handle. In addition, despite the sterilization, there is still a danger of contamination by pyrogens generated by impurities resulting from the assembly of numerous complex surfaces. Finally, the lubrication of the compaction and ejection chamber, which forms an integral part of the cartridge, is not optimal, since there is presently no known surface treatment or lubricant that is stable during vapor sterilization and/or during prolonged immersion in the storage liquid.

The document BE 1 016 692 describes another injection device which eliminates the manual compaction operation (folding or rolling) prior to the injection, this compaction of the IOL being produced by the action of the pusher of the injector. According to said document, the cartridge in which the IOL is stored in the non-stressed state is shaped like a funnel connecting to an output cannula. It is provided with retention means which ensure that it is held in a storage receptacle, and with means for fastening it on the free end of the injector. After the surgeon has opened the receptacle containing the cartridge, it suffices to snap-fit the cartridge onto the injector and act on the pusher.

This design is able to overcome a number of the disadvantages mentioned above, since the injector body is packed in a dry package sterilized by ethylene oxide gas and, therefore, it is dry when the surgeon takes hold of it. Moreover, the package is lighter. However, the pre-loaded cartridge is stilled packed, sterilized and stored in a moist package containing a storage liquid, which leaves the problem regarding the stability of its surface coating and/or its lubrication. For this reason, at the time of its use, the cartridge containing the pre-loaded IOL has to undergo multiple rinses with a balanced saline solution in order to avoid post-operative inflammation.

The present invention aims to overcome this disadvantage and make available a device for injection of a foldable intraocular lens, in which the need for prior rinsing is suppressed and which is reliable. The underlying concept of the invention is in particular to dissociate the storage cartridge of the IOL from the compaction and ejection chamber, which can then be subjected to sterilization by ethylene oxide gas to ensure the stability of its surface coating and/or of its lubrication. To this end, the invention relates to an injection device for a flexible intraocular lens, comprising an injector body accommodating a sliding pusher, and a compaction and ejection chamber rigidly connected to said injector body, characterized in that the compaction and injection chamber is articulated on the distal end of the injector body so as to be able to adopt two positions, on the one hand a position called the loading position, in which at least a part is folded along the injector body transversely offset with respect to the longitudinal axis of the injector body in such a way that a cartridge containing an intraocular lens in the non-stressed state can be loaded into the injector body along said longitudinal axis, and, on the other hand, a position called the injection position, in which the compaction and injection chamber is locked in the continuation of said injector body.

This injection device according to the invention makes it possible, by folding at least a part of the compaction and ejection chamber (articulated functional part which participates in the compaction and injection of the lens) along the injector body (against same), to leave room in the injector body for loading a cartridge (which was previously stored apart in a sterile receptacle) in the continuation of said body.

The (movable) functional part of the compaction and ejection chamber being offset laterally with respect to the longitudinal axis of the body (arranged adjacent to the injector body), it does not participate in the operation of loading the cartridge on the body, which operation is liable to produce mechanical stresses on the elements involved in the operation. If the functional part of the compaction and ejection chamber participated in this loading operation, it would be affected by such mechanical stresses. It could then suffer deformation of such a nature as to disturb the subsequent operation of compaction and ejection of the lens (e.g. lack of alignment of the axis of insertion of the lens during this operation), with all the risks and consequences that may be imagined. Furthermore, the axis of articulation of the chamber or of a part thereof is orthogonal with respect to the longitudinal axis of the injector body and offset transversely with respect to this axis. Thus, when the compaction and ejection chamber is locked in the continuation of the injector body, there is no risk that the thrust exerted on the sliding pusher will create a moment of inertia capable of causing a rotation of the cartridge/chamber assembly (the locking is in fact designed to provide a locked assembly in an irreversible manner, which increases the reliability of the device). The device according to the invention is therefore particularly reliable. It will be noted that the compaction and ejection chamber, or the movable part thereof, can also be locked in the loading position.

According to a preferred embodiment, the injection device for a flexible intraocular lens according to the invention is characterized in that the distal part of the injector body has a reception chamber for the cartridge, and in that the injector body carries what is called an alternating locking means which is able to occupy two successive blocking positions, namely a first position which blocks the movement of the pusher when the compaction and injection chamber is in the cartridge-loading position, then a second position which blocks (locks) the compaction and ejection chamber in the injection position in the continuation of the injector body and instantaneously frees (unlocks) the sliding pusher, which can then be actuated. Thus, one and the same locking means is able to ensure two different types of locking (two distinct functions) for the two respective consecutive positions of the compaction and ejection chamber. By manipulating the locking means, a user can easily pass successively and irreversibly from the first blocking position to the second blocking position, without being able to return to the first position. This mechanism ensures the safety and reliability of the use of the device at a later stage of preparation (locking means primed) and guarantees the unique nature of its use ("one-off use"). Indeed, an incorrect preparation of the injection (for example on account of an injection device that lacks reliability) may cause an incident during the injection, which will require a larger incision to be made in order to withdraw the damaged implant.

According to one possible feature of the invention, the alternating locking means is able to slide along the injector body in order to pass irreversibly from the first blocking position to the second, which permits an easy displacement of the locking means by a simple movement on the part of a user.

According to another possible feature of the invention, the alternating locking means comprises a grip portion for a user and two portions which are arranged at the two opposite ends, i.e. proximal and distal ends, of said locking means, and which are able to cooperate respectively with the sliding pusher and with the compaction and ejection chamber (for example via snap-fitting means provided on the chamber) in order to lock the latter irreversibly to the body of the injector (the cartridge containing the lens is imprisoned in the compaction and ejection chamber perfectly in the axis of the injection). The locking means is thus of a particularly simple and effective design. On account of the laterally offset position of at least one part of the compaction and ejection chamber (part which participates in the compaction and injection of the lens) during the loading of a cartridge, said at least one part of the chamber is not affected.

According to other possible features of the invention taken singly or in combination with one another:
- the alternating locking means has the general form of a rider provided with tabs that are intended to guide the sliding of said rider in lateral grooves formed on the longitudinal sides of the injector body;
- the rider carries, at its proximal part, a curved bolt cooperating with an opening of the pusher;
- the distal part of the rider carries a tongue which projects forward and, in the second blocking position, is intended to engage on a proximal portion of the compaction and ejection chamber in order to block the latter in the closed position; at this stage, only the movement of the sliding pusher with a view to compaction and injection is possible;
- near its distal end, the lower face of the tongue of the rider has a groove intended to cooperate with snap-fitting means arranged on the compaction and ejection chamber;
- the compaction and ejection chamber has a proximal part mounted fixedly on the injector body, and a distal part which is articulated on the proximal part via a hinge (e.g. flexible), the axis of the hinge being orthogonal with respect to the longitudinal axis of the injector body and offset transversely with respect to said longitudinal axis; the distal part forms the articulated functional part of the chamber, whereas the proximal part, which is a frame for example, serves as a mechanical support to the distal part for its movement of rotation about the axis of the hinge; according to one variant, the chamber is made as a single part articulated via a hinge on the distal end of the injector body, the axis of the hinge being orthogonal with respect to the longitudinal axis of the injector body and offset transversely with respect to said longitudinal axis;
- the injector body carries a bow, of which the bottom and the front face have a receiving slit in which an end cannula of the compaction chamber is accommodated when said chamber is in the loading position;
- the injector body has, on its upper face, a slot in which the curved rear bolt carried by the locking means can engage;
- the injector body is provided with two finger supports and with two abutments placed in front of said supports;
- the injector body (or the fixed part of the compaction and ejection chamber) is provided with a securing or retaining member (e.g. groove) intended to cooperate with snap-fitting means arranged on the compaction and ejection chamber;
- the pusher comprises a proximal part, of which the proximal end is provided with a finger support, an intermediate part of smaller cross section, and a distal pusher head, of which the cross section matches that of the internal cavity of the cartridge;
- a stub made of deformable material is interposed between the head of the pusher and the proximal opening of the cartridge;
- the upper edge of the proximal opening of the compaction and ejection chamber is provided with snap-fitting means in the form of tongues of which the free end is shaped like an arrow head, the barbs of this arrow head cooperating with the groove of the rider and with a member for securing the distal end of the injector body when the compaction and ejection chamber is in the injection position; this blocking position being irreversible at this stage, only the movement of the sliding pusher with a view to compaction and injection is possible;
- the lateral faces of the cartridge have removable catches or non-removable catches (for example bosses) for holding the intraocular lens in translation;
- the cartridge carries a projecting element (e.g. tongue) which is able to cooperate with the compaction and ejection chamber when the latter is in the injection position in order to block the cartridge in translation. The projecting element abuts against a proximal portion of the distal part of the compaction and ejection chamber in order to prevent the translation thereof to the front of the device, that is to say away from the pusher. The projecting element of the cartridge (for example arranged along the longitudinal axis of the cartridge) also serves to keep it in a vertical position in a housing situated in a sterile receptacle that is intended to enclose said cartridge until the latter is loaded into the injection device according to the invention. It will be noted that the sterile receptacle has an opening sufficiently wide to receive the distal end of the device with the compaction and ejection chamber arranged in the folded position against the injector body (in a lateral position arranged along an axis parallel to the longitudinal axis of the body but distinct therefrom) for the purpose of loading the cartridge into the body along the longitudinal axis thereof.

According to an aspect that may be independent of the device described above, the invention also relates to a cartridge as disclosed briefly above and to a sterile receptacle for the storage of such a cartridge.

It will be noted that the invention also relates to an injection assembly which comprises the injection device as disclosed above (this device comprises the injector body housing the pusher and the compaction and ejection chamber) and a cartridge containing an intraocular lens (implant). The features mentioned above also apply to the injection assembly.

Other features and advantages of the invention will become clear from the following description of non-limiting embodiments of the invention, with reference to the attached drawings in which:

FIG. 1a is a general perspective view of the front of an injector device for a flexible intraocular lens according to the invention, before locking of the compaction and ejection chamber;

FIG. 1b is a general profile view of the injector device of FIG. 1a after locking of the compaction and ejection chamber;

FIG. 2a is a view similar to FIG. 1a, the locking and ejection chamber being open and the cartridge containing the intraocular lens being loaded in the reception chamber of the distal part of the body of the injector;

FIG. 2b is a general profile view of the injector device of FIG. 2a;

FIG. 3 is an exploded perspective view of the pusher and of the cartridge in the position of alignment inside the injector body;

FIG. 4 is an enlarged perspective view of the alternating locking means carried by the injector body;

FIG. 5a is an enlarged perspective view of the compaction and ejection chamber in the open position without cartridge;

FIG. 5b is an enlarged perspective view of the compaction and ejection chamber in the open position, showing the relative position of the cartridge with respect to this chamber when it is held by the injector body;

FIG. 5c is an enlarged perspective view of the compaction and ejection chamber in the closed position;

Figure 6A:
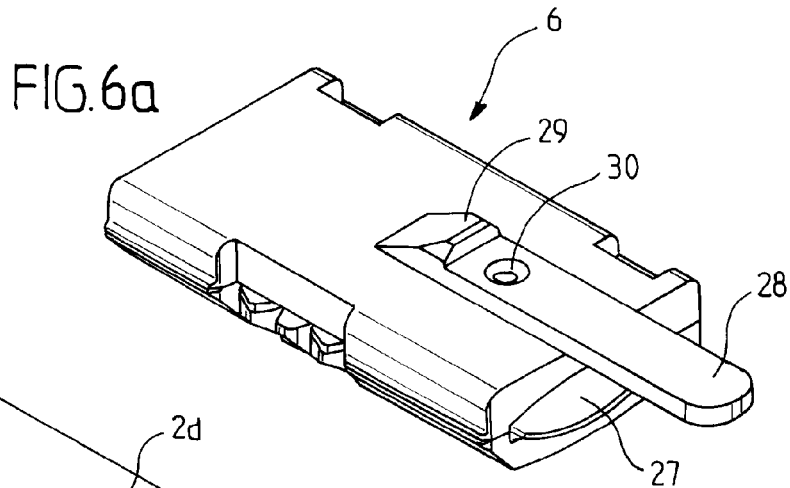
FIG. 6a is an enlarged perspective view of the cartridge without intraocular lens.

In the various figures, elements that are identical or that have analogous functions are indicated by the same reference signs.

In FIGS. 1a, 1b, 2a and 2b, it will be seen that the injector is composed of an injector body 1, a pusher 2 engaged in the injector body 1 at the proximal end of the latter, a compaction and ejection chamber 3, and a lock 4. The compaction and ejection chamber is mounted rotatably on the distal end of the injector body 1 in such a way as to be able to be folded along the latter in order to free the access to a reception chamber 5 (FIG. 2a) designed to receive a cartridge 6 containing an intraocular lens 7 in the non-stressed state. The injector body 1 is provided with two finger supports 8 and with two abutments 9 placed in front of said supports in order to ensure a secure and comfortable grip for the user, without risk of the latter applying untimely pressure to the pusher. This arrangement is particularly useful during the manipulations needed for placing the cartridge in the injector. The injector body 1 also carries a bow 10, of which the bottom and the front face have a receiving slit in which the end cannula 25 of the compaction and ejection chamber 3 is received when said chamber is tilted into the open position (position for loading a cartridge), as will be seen in FIGS. 2a and 2b. On its upper face, the injector body 1 has a slot 12 in which a curved rear bolt 13 carried by the lock 4 can engage. Whereas the injector body 1 and the pusher 2 are preferably made of a synthetic material such as polycarbonate or ABS, the compaction and ejection chamber 3 and the cartridge 6 are preferably made of a polymer material that is compatible with vapor-phase sterilization, for example polypropylene.

In FIG. 3, it will be seen that the pusher 2 comprises a proximal part 2a, of which the proximal end is provided with a finger support 14, an intermediate part 2b of smaller cross section, and a pusher head 2c, of which the cross section matches that of the internal cavity of the cartridge 6. On its upper face, the pusher head 2c has a hollow or a slot 15 intended to receive the curved rear bolt of the lock 4. In the embodiment shown here, between the head 2c of the pusher 2 and the proximal opening of the cartridge 6, a stub 2d made of deformable material is interposed which is intended to transmit the thrust of the pusher 2 to the intraocular lens 7 without risk of damaging it. The stub 2d has a cross section similar to that of the internal cavity of the cartridge 6. The proximal part 2a of the pusher 2 is provided with a catch 2e intended to prevent accidental disengagement of the pusher 2 from the injector body 1.

It will be seen from FIG. 4 that the alternating locking means 4 has the general form of a rider provided with tabs 16 that are intended to guide the sliding of said rider in lateral grooves 17 formed on the longitudinal sides of the injector body 1. The distal part of the rider 4 carries a tongue 18 projecting out to the front. The tongue 18 blocks the compaction and ejection chamber 3 when the latter is in the closed position (injection position). The rear of the tongue 18 is thickened in such a way as to form a finger support making it easier to move the rider to its position in which it locks the compaction and ejection chamber 3. The sliding of the rider 4, to its position in which it blocks the compaction and ejection chamber 3, frees the curved bolt 13 from the opening 15 in the head 2c of the pusher 2, thereby permitting the displacement of said pusher. Near its distal end, the lower face of the tongue 18 has a groove 19 intended to cooperate with snap-fitting means 21 arranged on the compaction and ejection chamber 3. The front delimiting edge of the tongue 18 has an opening 20 for the passage of a needle for injecting a biocompatible viscoelastic lubricating product into the compaction and ejection chamber 3.

In FIGS. 5a and 5b, the compaction and ejection chamber 3 is shown in the open position (loading position). It comprises a fixed proximal part such as a frame 22 intended to engage by friction on the distal end of the injector body 1. Two catches 23 ensure that the frame 22 is held by engagement in grooves provided for this purpose in the outer lateral walls of the injector body 1. The compaction and ejection chamber 3 comprises a functional distal part (serving for the compaction and injection of a lens), which is articulated on the frame 22 via a flexible hinge 24, of which the axis is orthogonal with respect to the longitudinal axis of the injector body 1 and offset transversely with respect to said longitudinal axis (horizontal axis situated below the body 1). The distal part of the compaction and ejection chamber 3 is shaped like a funnel connecting to an outlet cannula 25. The inner lateral faces of the frame 22 are provided with grooves 26 for reinforcing the frictional hold of the frame 22 on the distal end of the injector body 1. The upper edge of the proximal opening of the distal part of the compaction and ejection chamber 3 is provided with snap-fitting means 21 in the form of tongues, of which the free end is shaped like an arrow head, the barbs of this arrow head cooperating, on the one hand for the upper lugs, with the groove 19 of the rider 4 (groove formed in the lower face of the rider) and, on the other hand for the lower lugs, with a member 1a (FIG. 2a) for securing or retaining the distal end of the injector body 1 when the compaction and ejection chamber 3 is closed (it will be noted that the securing or retaining member can alternatively be provided on the fixed part of the chamber 3, for example the frame 22). This therefore results in a positive locking of the distal (movable) part of the compaction and ejection chamber 3 firstly on the injector body 1, by snap-fitting on the securing or retaining member 1a, then with the rider 4, when the latter is displaced.

When the rider 4 is pushed forward, it pulls the curved bolt 13 out of the groove 15. The movement of the pusher 2, which was hitherto impossible on account of the presence of the bolt in the groove, is therefore possible only when the rider 4 has effectively been placed in the position in which it blocks the compaction and injection chamber in the closed position.

Figure 6B:
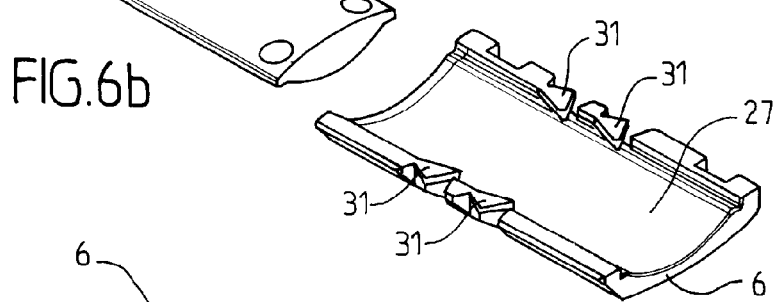
FIG. 6b is an enlarged perspective view of the bottom of the cartridge.
Figure 6C:
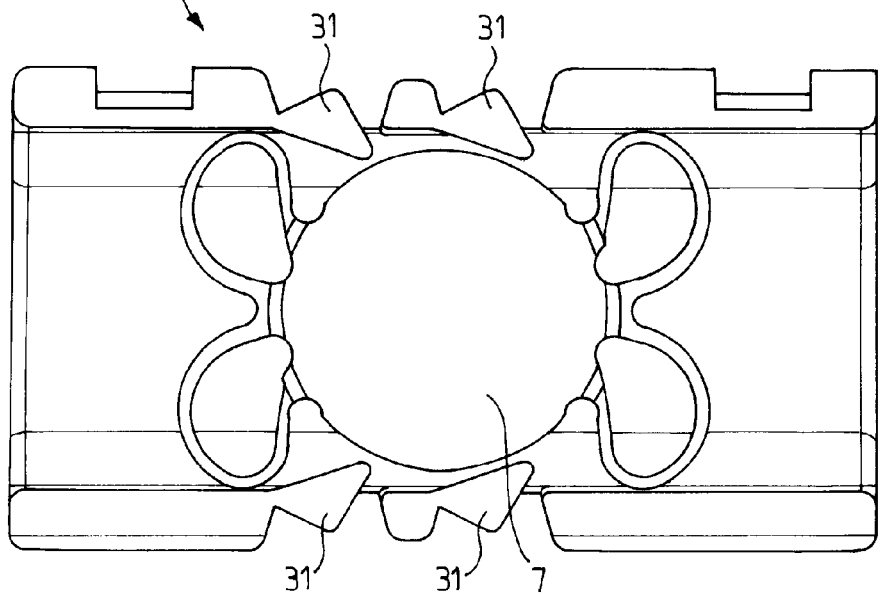
FIG. 6c is an enlarged top view of the bottom of the cartridge, illustrating the non-stressed storage position of an intraocular lens.

In FIGS. 6a, 6b and 6c, it will be seen that the cartridge 6 is of a general parallelepipedal shape and that its internal walls define a receiving cavity 27 for an intraocular lens 7. The upper face of the cartridge 6 carries a projecting element, such as a projecting tongue 28, of which the rear end forms a hook 29. Near the hook 29, a hole 30 permits the passage of a needle for injecting a biocompatible viscoelastic lubricant into the cavity 27. The tongue 28 has a dual function: it keeps the cartridge 6 in the vertical position in its storage receptacle and it engages on the proximal part of the distal part of the compaction and ejection chamber 3 in order to block the cartridge in translation when the compaction and ejection chamber is in the closed position (ejection position). Advantageously, as is shown in FIGS. 6b and 6c, the lateral faces of the cartridge 6 have catches 31 which ensure that the implant 7 is held in translation. The catches 31 are preferably formed in one piece with the cartridge 6. Alternatively, the removable catches can be replaced by (fixed) davits.

Figure 7B:
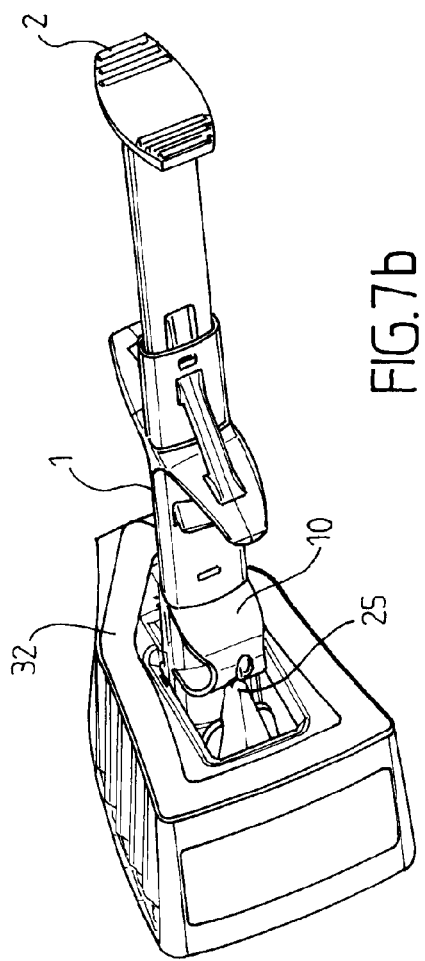
FIG. 7b is a perspective top view illustrating the introduction of the injector device into the package of FIG. 7a for loading the cartridge.
Figure 7A:
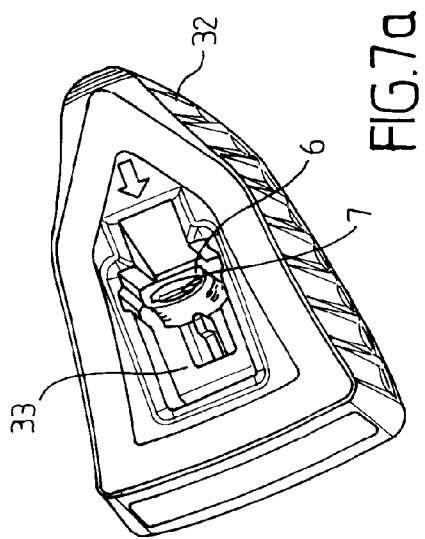
FIG. 7a is a perspective top view of a receptacle for storage of the cartridge.
Figure 8:
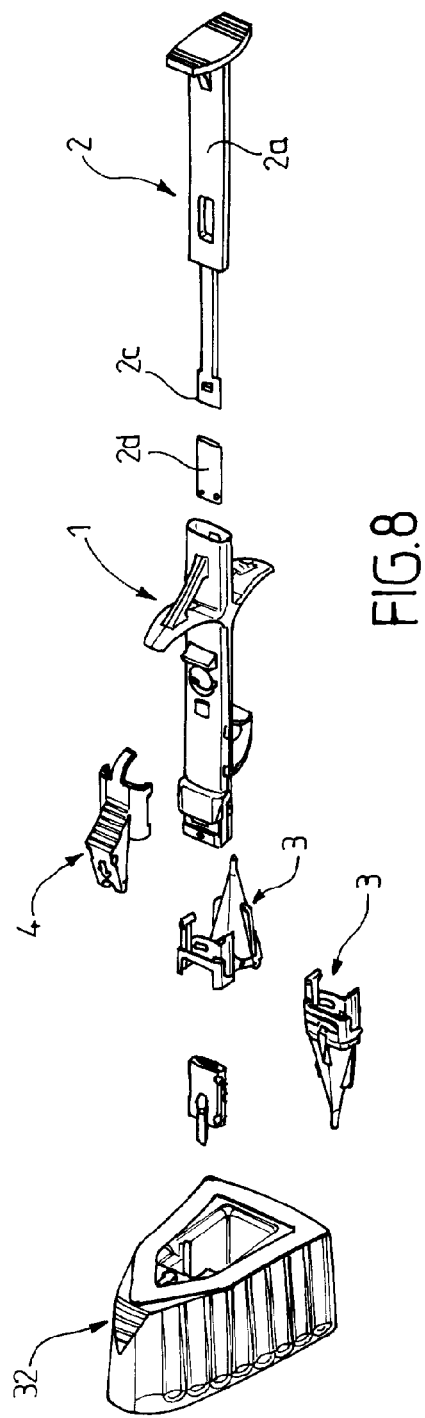
FIG. 8 is an exploded perspective view of the component elements of an injection assembly according to the invention, the cartridge being shown in the open condition and in the closed condition.

FIGS. 7a and 7b shown an embodiment of a sterile package or receptacle specially designed for storing a cartridge 6 and inserting it into the injector body 1 at the time of use. It will be seen that this package 32 has a wide well 33 in which the cartridge 6, inside which an IOL 7 is accommodated, is held in a vertical position substantially at the center of the well 33. On each side of the cartridge 6, a sufficient space is formed to receive the distal end of the injector in the open position, the compaction and ejection chamber 3 being folded along the injector body 1. It will be appreciated that the cartridge 6 can thus be stored in a state immersed in a saline aqueous environment and kept sterile until the time of use by closure of the package 32, for example by a detachable cap. During use, the assembly according to the invention allows the surgeon to be ready to inject the IOL by performing only three movements, without risk of damaging the IOL, affecting its sterile state or getting the fingers wet: namely engaging the injector on the cartridge for loading the latter, closing the compaction and ejection chamber, locking the compaction and ejection chamber in the closed position with simultaneous release of the pusher.

Although the invention has been described in connection with a number of specific embodiments, it is clear that it is not in any way limited to these and that it encompasses all the technical equivalents of the means described, and also the combinations thereof, as covered by the scope of the invention.

The invention claimed is:

1. An injection device for a flexible intraocular lens, comprising an injector body accommodating a sliding pusher, and a compaction and ejection chamber rigidly connected to said injector body, characterized in that the compaction and injection chamber is articulated on the distal end of the injector body so as to be able to adopt two positions, on the one hand a position called the loading position, in which at least a part of the compaction and injection chamber is folded along the injector body transversely offset with respect to the longitudinal axis of the injector body in such a way that a cartridge containing an intraocular lens in the non-stressed state can be loaded into the injector body along said longitudinal axis, and, on the other hand, a position called the injection position, in which the compaction and injection chamber is locked in the continuation of said injector body, wherein the distal part of the injector body has a reception chamber for the cartridge, and in that the injector body carries what is called an alternating locking means which is able to occupy two successive blocking positions, namely a first position which blocks the movement of the pusher when the compaction and injection chamber is in the loading position, then a second position which blocks the compaction and ejection chamber in the injection position in the continuation of the injector body and frees the pusher.

2. The injection device as claimed in claim 1, wherein the alternating locking means is able to slide along the injector body in order to pass irreversibly from the first blocking position to the second.

3. The injection device as claimed in claim 2, wherein the alternating locking means comprises a grip portion for a user and two portions which are arranged at the two opposite ends, a proximal end and a distal end, of said locking means, and which cooperate respectively with the sliding pusher and the compaction and ejection chamber.

4. The injection device as claimed in claim 1, wherein the alternating locking means comprises a grip portion for a user and two portions which are arranged at the two opposite ends, a proximal end and a distal end, of said locking means, and which are able to cooperate respectively with the sliding pusher and the compaction and ejection chamber.

5. The injection device as claimed in claim 1, wherein the alternating locking means is a rider provided with tabs that are intended to guide the sliding of said rider in lateral grooves formed on the longitudinal sides of the injector body.

6. The injection device as claimed in claim 5, wherein the rider carries, at its proximal part, a curved bolt cooperating with an opening of the pusher.

7. The injection device as claimed in claim 6, wherein the injector body has, on its upper face, a slot in which the curved rear bolt carried by the locking means can engage.

8. The injection device as claimed in claim 6, wherein the distal part of the rider carries a tongue which projects forward and, in the second blocking position, is intended to engage on a proximal portion of the compaction and ejection chamber in order to block the latter in a closed position.

9. The injection device as claimed in claim 5, wherein the distal part of the rider carries a tongue which projects forward and, in the second blocking position, is intended to engage on a proximal portion of the compaction and ejection chamber in order to block the latter in the closed position.

10. The injection device as claimed in claim 9, wherein, near its distal end, the lower face of the tongue of the rider has a groove intended to cooperate with snap-fitting means arranged on the compaction and ejection chamber.

11. The injection device as claimed in claim 10, wherein the upper edge of the proximal opening of the compaction and ejection chamber is provided with snap-fitting tongues, of which the free end is shaped like an arrow head, the barbs of this arrow head cooperating with the groove of the rider and with a member for securing a distal end of the injector body when the compaction and ejection chamber is in the injection position.

12. The injection device as claimed in claim 1, wherein the compaction and ejection chamber has a proximal part mounted fixedly on the injector body, and a distal part which is articulated on the proximal part via a hinge, the axis of the hinge being orthogonal with respect to the longitudinal axis of the injector body and offset transversely with respect to said longitudinal axis.

13. The injection device as claimed in claim 1, wherein the injector body carries a bow, of which the bottom and the front face have a receiving slit in which an end cannula of the compaction and ejection chamber is accommodated when said chamber is in the loading position.

14. The injection device as claimed in claim 13, wherein the injector body is provided with two finger supports and with two abutments placed in front of said supports.

15. The injection device as claimed in claim 1, wherein the pusher comprises a proximal part, of which the proximal end is provided with a finger support, an intermediate part of smaller cross section, and a distal pusher head, of which the cross section matches that of an internal cavity of the cartridge.

16. The injection device as claimed in claim 15, wherein a stub made of deformable material is interposed between the distal pusher head of the pusher and a proximal opening of the cartridge.

17. The injection device as claimed in claim 1, wherein the lateral faces of the cartridge have catches or bosses for holding the intraocular lens in translation.

18. The injection device as claimed in claim 1, wherein the cartridge carries a projecting element that cooperates with the compaction and ejection chamber when the latter is in the injection position in order to block the cartridge in translation.

19. An injection assembly for an intraocular lens, wherein said injection assembly comprises an injection device as claimed in claim 1 and a cartridge containing an intraocular lens in a non-stressed state.

* * * * *